United States Patent [19]
Carstairs et al.

[11] Patent Number: 5,817,600
[45] Date of Patent: Oct. 6, 1998

[54] COMPOSITION FOR TREATMENT OF PLANT MATERIAL

[75] Inventors: Margaret L. Carstairs; Laurance W. I. Jennings, both of Fifc, Great Britain

[73] Assignee: British Technology Group Limited, London, England

[21] Appl. No.: 972,365

[22] Filed: Nov. 18, 1997

Related U.S. Application Data

[63] Continuation of Ser. No. 554,163, Nov. 6, 1995, abandoned.

[51] Int. Cl.$^6$ .................................................. A01N 43/90
[52] U.S. Cl. ........................................... 504/115; 504/136
[58] Field of Search ................................... 504/115, 136, 504/241

[56] References Cited

U.S. PATENT DOCUMENTS

| | | | |
|---|---|---|---|
| 3,640,696 | 2/1972 | Goldmann | 71/9 |
| 4,337,080 | 6/1982 | Szkrybalo | 71/88 |
| 4,472,186 | 9/1984 | von Haartman | 71/63 |
| 5,549,729 | 8/1996 | Yamashita | 71/26 |

FOREIGN PATENT DOCUMENTS

| | | |
|---|---|---|
| 1 164 744 | 3/1964 | Germany . |
| 1002867 | 7/1965 | United Kingdom . |

OTHER PUBLICATIONS

Chemical Patents Index, Documentation Abstract Journal, Section Ch, Week 9033, Derwent Publications Ltd., London, GB, Class E, AN 250699, & JP A, 2174 701 (Kyowa Hakko Kogyo KK) 6 Jul. 1990.

G.N. Rao, "Delaying of petal senescence . . . "Chemical Abstracts, vol. 98 No. 21, 23 May 1983, Columbus, Ohio, US, Abstract #174772s, p. 268.

Y. Saks et al. "Effect of gibberillic acid on carnation . . . " Plant Growth Regulation, vol. 11, 1992, NL, pp. 45–51.

W.G. Doorn et al. "Effect of exogenous hormones . . . "Plant Growth Regulation, vol. 11 1992, pp. 56–62.

G.M. Felippe "Promotion of rooting in stem cuttings . . . "Revta. Brasil, Bot., vol. 2, 1979, BR, pp. 73–76.

S.M. Ahmad. "In vitro regeneration of *Bryum gametophore* . . . "Science & Culture, vol. 52 No 4, 1985, pp. 137–139.

Hess, Dieter. *Plant Physiology*. Berlin:Springer–Verlag. pp. 304–305. 1975.

Considine, John A. "Concepts and practice of use of plant growth regulating chemicals in viticulture", chapter 6 in *Plant Growth Regulating Chemicals*, vol. I. Louis G. Nickell, ed. CRC Press. pp. 89–96. 1983.

Matthysse et al. "Functions of Hormones at the Whole Plant Level of Organization", chapter 6 in *Hormonal Regulation of Development II*. Tom K. Scott, ed. Berlin:Springer–Verlag. pp. 219–224. 1984.

*Primary Examiner*—S. Mark Clardy
*Attorney, Agent, or Firm*—Nixon & Vanderhye

[57] ABSTRACT

The invention relates to the use of one or more methyl xanthines to enhance the flower and foliage color of plant material and compositions therefor; compositions to promote the continued development of plant material comprising a methyl xanthine and a gibberellin; use of a composition comprising a methyl xanthine and a gibberellin to promote the continued development of plant material; and plant material treated with a composition as defined above

49 Claims, No Drawings

COMPOSITION FOR TREATMENT OF PLANT MATERIAL

This application is a continuation of application Ser. No. 08/554,163, Nov. 6, 1995 abandoned.

COMPOSITION

The present invention is concerned with the use of methyl xanthines to enhance the flower and/or variegated foliage colour of plant material.

Plant materials, especially flowers and foliage, are often short-lived once picked or harvested and may wilt rapidly after picking. To some extent, wilting of cut plant materials such as flowers and foliage may be prevented by placing the cut plant stems into water. Conventionally, water is added in the container or vase up to a depth of halfway to two-thirds of the way up the stem length (depending on foliage cover).

There continues to be a demand for cut plant material, such as flowers or foliage, for decorative purposes. However, one of the drawbacks of cut plant material is the short life-span of the material after harvesting. Various additives may be mixed into the vase water in order to delay the death of the plant material. These additives range from the simple inclusion of a teaspoon of domestic sugar (sucrose) to pre-prepared sachets of plant food. However, the commercially available plant food (such as "Chrysal") for cut plant material only slows down the rate of deterioration in the plant material. The plant material will not, however, continue to grow and/or develop and therefore immature buds frequently fail to open at all, even where the plant food is added to the vase water. Any buds that do open are generally deficient in colour and usually fail to develop to the same depth of colour as those buds of uncut flowers; in addition the life of the bloom and its colour stability during that period is greatly diminished. Moreover, many commercially available plant foods, such as "Chrysal", cannot be used in crystal glass containers and must be made up in warm water to ensure dissolution of the plant food.

There is, therefore, a need for a plant treatment composition having the ability to enhance the flower and/or variegated foliage colour, promote the continued development and preferably increase the longevity of harvested plant material. The present invention addresses these needs.

In a first aspect of the present invention there is provided a composition for enhancing the flower and/or variegated foliage colour of plant material which comprises one or more methyl xanthines. The composition is preferably in liquid form, especially in the form of an aqueous solution. The colour enhancing effects of the composition may be realised by spraying a solution of the composition onto the leaves and/or flowers of plant material or by immersing the cut stems or roots thereof in such a solution. Although use may, potentially, be made of any methyl xanthine it is preferred to use caffeine and/or theophylline due to their relatively low cost and ready availability. An example of the composition according to the first aspect of the invention comprises a methyl xanthine, preferably caffeine and/or theophylline. Thus, the colour of blooms exposed to solutions containing methyl xanthines is generally more intense; the development of colour is also observed in emerging flowers, notably those from secondary and tertiary buds; and the rate of colour loss is inhibited. The term "enhance" is to be understood to include any one, a combination or all of the following: the development of colour in unopened flower buds, increasing or promoting the depth of colour of open coloured blooms and/or variegated foliage, stabilising the colour and prolonging the period of pigmentation over the lifetime of the bloom. The term "variegated foliage" is to be understood to include plant material other than blooms wherein the plant material is characterised by more than one colour. In many cases this will include the green colour imparted to the foliage by the chlorophyll contained in the plant. The other colours arise from the presence of plant pigments.

Gibberellins are plant hormones which are known to have certain effects on plant development. Horticultural applications of the gibberellins include promotion of the growth of large, seedless grapes, the promotion of the germination of sunflower seeds and the prevention of ripening in citrus fruits.

Gibberellic acid, which is a specific member of the gibberellin group of plant hormones, is destroyed by chlorine. Thus, any gibberellic acid added to tap water will be totally destroyed within hours since tap water contains chlorine which is added to control bacterial growth. Thus, it has not previously been recognised that gibberellins have a general effect on plant materials which ensures their continued development after harvesting.

In a second preferred aspect of the present invention there is provided a composition for enhancing the flower and/or variegated foliage colour of and promoting the continued development of plant material which comprises one or more methyl xanthines and a gibberellin. Preferably the methyl xanthine is caffeine and/or theophylline. An example of a composition according to the second aspect of the invention comprises caffeine and/or theophylline and a gibberellin. Caffeine and/or theophylline are preferably present in an amount from 0.15 to 0.50%, conveniently from 0.15 to 0.20%, of the undiluted composition and 15 to 20 ppm in the diluted composition.

A preferred gibberellin is gibberellic acid and a particularly preferred form of gibberellic acid is the isomer known as $GA_3$. Other isomeric forms of gibberellic acid may, however, also be used in the composition according to the invention. Optionally the composition may contain a mixture of two or more different isomers of gibberellic acid. It is preferred that the gibberellin comprises 0.005 to 0.30% by weight of the undiluted composition. When diluted with water, the gibberellin is preferably present at a concentration of 1 to 30 ppm, more preferably 1 to 10 ppm and especially 5 to 10 ppm, of the diluted composition.

By the term "continued development" it is to be understood that the plant material treated according to the present invention has superior post-harvest flowering or growth compared to non-treated or conventionally treated plant material. Where the plant material is already in full flower or is otherwise not in a state of growth, the present invention is able to maintain the treated plant material in the same state as at the time of harvest for a longer period than would be possible with conventional treatments. Thus, the effects of the present composition include increased florescence (greater degree of flowering), increased growth, a decreased rate of post-harvest deterioration and decay and increased longevity of the plant material.

In the particular case where plant material is harvested with very immature buds, such buds frequently fail to mature into opened flowers following harvest and if the buds do open the opened flowers are usually deficient in colour. However, where the plant material is treated in accordance with the present invention the development of colour in, successful opening and preferably the maturation of such buds is greatly promoted. This effect is especially noticeable in long stemmed multi-bud flowers such as freesias where the uppermost (and youngest) buds can achieve a much greater degree of opening than with the untreated stems.

The compositions according to the invention also have the advantages that they can be used in crystal glass vases without any detrimental effect; they can be made up in water at any temperature, even cold water.

Where the composition according to the invention is to be used in ordinary tap water, for example in domestic use, it is essential that a "chlorine sweep" is included in the composition. However, if the composition is to be added to distilled water or to other non-chlorinated water (for example well water or spring water) then the chlorine sweep is not an absolute requirement.

The term "chlorine sweep" is used herein to refer to any agent which has the ability to remove free molecular chlorine, so reducing the gibberellic acid-destroying effect. Suitable "chlorine sweeps" include sodium metabisulphite and sodium sulphite. The "chlorine sweep" is added in quantities necessary to remove any free molecular chlorine from the water to be used to make up the composition according to the invention. Suitable amounts have been found to be from 1.5 to 3.5% of the undiluted composition and from 5 to 500 ppm of the diluted composition.

In a third aspect, the present invention provides a composition to enhance the flower and/or variegated foliage colour and to preferably promote the continued development of plant material which is in contact with tap water, said composition comprising one or more methyl xanthines, gibberellic acid and a chlorine sweep. Preferably the composition according to the third aspect of the present invention comprises caffeine and/or theophylline, the gibberellic acid $GA_3$ and sodium metabisulphite as a chlorine sweep.

The term "plant material" is used above and hereinafter to any plant part attached to or detached from the plant as a whole. In particular, this phrase covers flowers, flower heads, flower-bearing stems, stems, leaves, leafy stems and stems bearing leaves, roots, tendrils, seeds, fruits and/or any other portion of a plant.

Optionally, the composition of the present invention may further comprise an osmotic pressure regulator. Such osmotic pressure regulators are intended to make the composition according to the invention, when diluted, isotonic with the cell sap of the plant material to be treated. Suitable osmotic pressure regulators include low molecular weight saccharides. For instance, a simple sugar, for example a mono or disaccharide (such as glucose or sucrose), is suitable for this purpose and is convenient for reasons of cost. Other examples include fructose, trioses such as maltotriose, glucose hydrates such as mannitol and sorbitol, and polyols such as pentaerythritol, or derivatives or mixtures thereof. The osmotic pressure regulator may comprise from 75 to 98% of the undiluted composition. Suitable concentrations in the diluted composition are 2 to 20 g/liter (2000 to 20000 ppm).

A pH regulator, such as an acid, preferably an organic acid, may also be included. Advantageously, the pH of the composition should be in the range of from 3.5 to 7, preferably from 3.5 to 5.5, to mimic the pH of plant sap. A low pH of this type will also restrict bacterial growth. Examples of suitable organic acids include citric, acetic, tartaric, propionic and lactic acids. Other organic acids are, of course, well-known to those skilled in the art. Alternatively, a compound which generates an acid "in situ" may be used or a very small quantity of a mineral acid. When an organic acid is used, suitable amounts are from 0.05 to 5.00% by weight of the undiluted composition depending on the dissociation constant of the chosen acid or mixture of acids.

Additionally, buffers such as sodium acetate, calcium lactate, potassium sodium tartrate and potassium hydrogen phosphate may be included in the composition to help maintain pH at a suitable level. However, in hard water areas where the level of calcium in the water is already high, it is preferred that the buffer is not a calcium salt, such as calcium lactate. In such circumstances, potassium sodium tartrate is a preferred buffer.

Other additives include calcium ions, vitamin substrates (such as mannitol and myo-inositol), nitrate or ammoniacal nitrogen, potassium ions, phosphates, amino acids (such as glycine), camphor and biocides, such as fungicides (such as carbendazim), antibiotics and bactericides (such as sodium chlorocyanurate, para-nitrophenol, sodium thioglycollate, benzoic acid, salicylic acid, oxine and anthraquinone) and yeast inhibitors such as nystatin.

It may be desirable to further include an agent which absorbs or otherwise removes ethylene gas. Ethylene is produced by plants and acts as an ageing (or ripening) agent. One suitable ethylene removing agent is camphor.

It is especially desirable that heavy metals, that is, metals heavier than aluminium, are not present in the composition of the present invention. In this regard chelating agents, such as EDTA (ethylenediaminetetraacetic acid) or DTPA (diethylenetriaminepenta-acetic acid) or the sodium, potassium or calcium salts thereof, may be added to remove any contaminating heavy metals which may be present in the water making up the composition. Preferably, the chelating agent is present in an amount up to 0.2 g/liter (200 ppm). A flocculent such as aluminium sulphate, may also be added to keep the vase water clear and transparent.

Although it is generally desirable to avoid the presence of heavy metals, as defined above, some elements are necessary for plant function and growth when connected to a root system and may still have beneficial effects even with cut flowers. Such elements are known as trace elements since they are generally present in trace amounts. It is envisaged that the following trace elements could be added as their salts to give the following concentrations in the diluted composition according to the invention:

| | |
|---|---|
| Boron | 0.003 ppm |
| Copper | 0.003 ppm |
| Iron | 0.030 ppm |
| Magnesium | 0.020 ppm |
| Manganese | 0.003 ppm |
| Molybdenum | 0.003 ppm. |

In some areas, fluoride is added to water in the form of sodium fluoride at a level of about 1 ppm. Fluoride ions are known to damage cut flowers by causing brown discolourations. Two major effects of fluoride ions are known. First, fluoride ions can cause a massive exodus of calcium ions from the cells of a plant thereby producing an upset in the osmotic balance in the cells. Secondly, fluoride ions react irreversibly with adenosine triphosphate the reactions of which are the base for all cellular syntheses. Accordingly, it is clearly desirable to remove fluoride ions from water that is to be used with the composition of the invention. It is therefore envisaged that the composition of the present invention may further comprise a fluoride ion scavenger. Suitable fluoride ion scavengers include calcium gluconate, ion exchange resins, adenosine triphosphate and alizarin dyes, such as alizarin-S, which are specific for fluoride ions. The use of calcium gluconate is especially preferred since this may also serve as a buffer.

In the case of daffodils and narcissi, it is current practice not to mix these flowers with other cut flowers because the cut daffodil/narcissus stem exudes a substance which is, in effect, toxic to other cut flowers. This substance is a mucilaginous slime which adversely affects other flowers by, inter alia, blocking the vascular system by which liquids are conveyed within the xylem. However, the mucilaginous exudate is a mixture of polysaccharides such as hemicelluloses, pectins and gums and can therefore be digested by certain enzyme preparations. Accordingly the composition may further comprise an enzyme preparation. Suitable enzyme preparations include those of plant origin commonly used to degrade polysaccharides in industrial applications. Mixtures of enzymes capable of breaking the $\alpha$-(1→4), $\alpha$-(1→6), $\beta$-(1→4), $\beta$-(1 →) linkages in such polysaccharides may be used with amylases and gluconases being particularly useful in this regard. Preferably, such enzymes are present in quantities of a few ppm in the diluted composition. A beneficial side-effect of the inclusion of such enzymes is that the polysaccharides are degraded to glucose and fructose which the cut flowers may then use as food or an osmotic pressure regulator.

The composition according to the invention may be in any convenient form, such as for example a powder, tablet, granules, solution or suspension. Generally powder or tablet forms of the composition are most convenient to transport or store until required. The powder or tablet may then be simply added to a predetermined volume of water and mixed in with stirring prior to use. Alternatively, the composition may be formulated into a liquid concentrate which can be diluted before use. The dilute and ready-to-use version of the composition also falls within the scope of the present invention. It is preferred that the dilute, ready-to-use composition contains 2–25 g/liter, preferably 5–20 g/liter, of the concentrated composition. Thus, the total concentration of the composition components in water is 2000 to 25000 ppm, preferably 5000 to 20000 ppm.

The water added to, or forming part of, the present invention is at a temperature of less than 50° C., for example 40° C. Desirably the water is at a temperature of from 2° C. to 32° C., such as 8° C. to 26° C.

The plant material is placed into a dilute aqueous form of the composition. The plant material is allowed to stand in the composition throughout its life. From time to time the volume of the composition may be topped up, as required.

The composition can be used for any type of cut or uncut plant material, especially commercial and garden flowers, shrubs, foliage, etc. The composition is particularly useful for cut flowers and shrubs, especially roses, irises, carnations, lilies, daffodils, sweet peas, freesias, poppies, orchids, chrysanthemums, lilac and eucalyptus, and Christmas trees. It is especially suitable for soft-stemmed flower varieties, such as anemones, phlox, sweet williams, etc., which normally have a notoriously short vase life. The composition of the invention may also be used on plant material that has been previously treated with the composition for sustaining plant material described in applicant's co-pending patent application which claims priority from British patent applications nos. 9309095.9 and 93 17063.7.

In a fourth aspect of the present invention there is provided a method of enhancing the flower and/or variegated foliage colour of and preferably promoting the continued development of plant material, said method comprising the steps of treating plant material with a composition as herein before defined. Preferably the composition is in liquid form, especially in the form of an aqueous solution. The composition may be sprayed onto the flowers or leaves of the plant material or, alternatively, the roots or cut stems may be immersed in a solution thereof. This method is especially suited to plant material watered with tap water or other forms of chlorinated water.

In accordance with the fourth aspect of the present invention there is provided a method which comprises treating the plant material with a composition comprising one or more methyl xanthines, preferably caffeine and/or theophylline, and a gibberellin such as gibberellic acid, as defined above. As a development of this fourth aspect of the present invention, a fifth aspect of the invention provides a method of enhancing the flower and/or variegated foliage colour of, preferably promoting the continued development of and sustaining plant material in contact with chlorinated water such as tap water, said method comprising treating said plant material with a composition comprising a methyl xanthine, preferably caffeine and/or theophylline, gibberellic acid and a chlorine sweep.

Viewed from yet a further aspect, the present invention provides a method of promoting the post-harvest development of plant material, said method comprising treating said plant materials after harvest with a composition comprising a methyl xanthine and a gibberellin, preferably caffeine and/or theophylline and gibberellic acid, as defined above. Again, where the said plant material is in contact with tap water or other chlorinated water, the composition comprises gibberellic acid and a chlorine sweep.

In a further aspect, the present invention provides plant material treated with a composition, as described above.

The invention is illustrated further by reference to the following, non-limiting, examples.

EXAMPLE 1

|  |  | % by weight |
|---|---|---|
| Sulphonated Polyester (Sulphonated Pentaerythritol) | 60 g | 82.94 |
| KNO$_3$ | 1.29 g | 1.78 |
| (NH$_4$)$_2$HPO$_4$ | 1.07 g | 1.48 |
| Gibberellic Acid (or GA$_3$) | 0.2 g | 0.28 |
| Citric Acid | 1.6 g | 2.21 |
| Tartaric Acid | 1.0 g | 1.38 |
| Mannitol | 3.0 g | 4.15 |
| Myo-inositol | 1.0 g | 1.38 |
| Glycine | 0.1 g | 0.14 |
| Sodium metabisulphite | 2.0 g | 2.76 |
| Calcium Gluconate | 1.08 g | 1.49 |
|  | 72.34 g |  |

The ingredients were admixed together and diluted before use to a concentration of 7 g/liter (i.e. 7 g of total composition listed above per liter of water).

EXAMPLE 2

|  |  | % by weight |
|---|---|---|
| Glucose | 100 g | 87.57 |
| KNO$_3$ | 1.29 g | 1.13 |
| (NH$_4$)$_2$HPO$_4$ | 1.07 g | 0.94 |

-continued

|  | % by weight |  |
|---|---|---|
| Gibberellic Acid (or GA$_3$) | 0.2 g | 0.18 |
| Citric Acid | 2.0 g | 1.75 |
| Tartaric Acid | 1.1 g | 0.96 |
| Mannitol | 3.0 g | 2.63 |
| Myo-inositol | 1.0 g | 0.88 |
| Glycine | 0.1 g | 0.09 |
| Sodium metabisulphite | 2.0 g | 1.75 |
| Camphor | 0.5 g | 0.44 |
| Calcium Lactate | 1.84 g | 1.61 |
| Carbendazim | 0.1 g | 0.09 |
|  | 114.2 g |  |

The ingredients were admixed together and diluted before use with water to a concentration of 11 g/liter.

EXAMPLE 3

|  | % by weight |  |
|---|---|---|
| Sorbitol | 50 g | 78.42 |
| KNO$_3$ | 1.29 g | 2.02 |
| (NH$_4$)$_2$HPO$_4$ | 1.07 g | 1.68 |
| Gibberellic Acid (or GA$_3$) | 0.10 g | 0.16 |
| Citric Acid | 2.0 g | 3.14 |
| Tartaric Acid | 1.1 g | 1.73 |
| Mannitol | 3.0 g | 4.71 |
| Myo-inositol | 1.0 g | 1.57 |
| Glycine | 0.1 g | 0.16 |
| Sodium metabisulphite | 2.0 g | 3.14 |
| Camphor | 1.0 g | 1.57 |
| Calcium Lactate | 1.0 g | 1.57 |
| Carbendazim | 0.1 g | 0.16 |
|  | 63.76 g |  |

The ingredients were admixed together and diluted before use with water to a concentration of 6 g/liter.

EXAMPLE 4

Twelve stems of *Lunaria annua* were carefully harvested just before flowering, and cut to the same length. The stems were divided into four lots and placed in flasks, each flask charged with 500 ml of one of the working solutions A, B, C or D.

Solution A (Control 1) contained only water and 0.02 g/liter of a biocide (sodium chlorocyanurate) to discourage bacterial growth.

Solution B (Control 2) contained:

| KNO$_3$ | 0.129 g/liter |
| (NH$_4$)$_2$HPO$_4$ | 0.107 g/liter |
| Citric Acid | 0.005 g/liter |

Solution C (Control 3) contained a commercial plant food (Chrysal) made up according to the instructions supplied.
Solution D (Test Solution) contained:

| Sucrose | 6 g/liter |
| KNO$_3$ | 0.129 g/liter |
| (NH$_4$)$_2$HPO$_4$ | 0.107 g/liter |
| Citric Acid | 0.005 g/liter |
| GA$_3$ | 0.010 g/liter |
| Biocide (Undecanoic acid) | 0.02 g/liter |

Citric or Tartaric acid was added to give a pH reading of 5.0 to 5.5 for the overall solution with a pH meter.

The flowering stems were examined daily and the final outcome noted.

RESULTS

In Control 1 (Solution A), the plants failed in five days. With Control 2 (Solution B), the plants remained green but showed some petal drop. In Control 3 (Solution C), the food did better than Control 2 but much less well than the test solution (Solution D) where the plants showed a 15% extension in terms of stem length, had more open florets and less petal fall. The results after 14 days are given in Table 1.

TABLE 1

| A CONTROL 1 | B CONTROL 2 | C CONTROL 3 | D TEST SOLUTION |
|---|---|---|---|
| Complete death of the stems. | Plants still green, some flowers remain (large petal fail). | Plants in reasonable condition, but some petal fall noticeable. | Plants 5 cm taller than originally cut. Good flowers, little petal fall. |

EXAMPLE 5

Forty-five stems of Iridaceae (Iris) in tight bud were split into three equal groups. Each group was placed in a flask charged with one liter of working solution and the flasks were maintained separately. One group (Group A) was placed in just water, one group (Group B) was placed in the test solution and, lastly, one group (Group C) was held in conditions believed to reflect current best practice (namely, the flowers were placed in water at 5 degrees centigrade containing "Chrysal"). The flowers were examined daily. The test was conducted in the absence of light for the first seven days. On day eight, the surviving flowers were transferred to a dimly lit room.

The test solution contained (per liter of water):

| Glucose | 10 g |
| Gibberellic Acid | 0.005 g |
| Citric Acid | 0.10 g |
| Mannitol | 0.3 g |
| Myo-inositol | 0.1 g |
| Glycine | 0.01 g |
| Sodium metabisulphite | 0.2 g |
| Sodium Methyl Salicylate | 0.2 g |
| Camphor | 0.025 g |
| Calcium gluconate | 0.030 g |
| KNO$_3$ | 0.129 g |
| (NH$_4$)$_2$HPO$_4$ | 0.107 g |
| Citric acid | 0.005 g |

The results are shown in Table 2 below. In this table, the expression "to damp off "means to rot" and, accordingly, the expression "damped off" means "rotting".

TABLE 2

| | NUMBER OF OPEN BLOOMS | | |
|---|---|---|---|
| DAY | 5° C. Water + "Chrysal" Best Current Practice (Group C) | 13° C. Test Solution (Group B) | 13° C. Water (Group A) |
| 1 | 0 | 0 | 0 |
| 2 | 0 | 0 | 0 |
| 3 | 0 | 2 | showing damage (starting to damp off) |

TABLE 2-continued

NUMBER OF OPEN BLOOMS

| DAY | 5° C. Water + "Chrysal" Best Current Practice (Group C) | 13° C. Test Solution (Group B) | 13° C. Water (Group A) |
| --- | --- | --- | --- |
| 4 | All open | All open | All damped off |
| 5 | All open | All open | — |
| 6 | All open | All open | — |
| 7 | Blooms curled at petal edges | All open | — |
| 8 | All damped off | All open | — |
| 9 | All damped off | Senescing | — |
| 10 | — | Senescing | — |

EXAMPLE 6

| | | % by weight |
| --- | --- | --- |
| Sucrose | 1000 g | 91.66 |
| Gibberellic Acid (GA$_3$) | 2 g | 0.18 |
| Citric Acid | 24 g | 2.20 |
| Tartaric Acid | 10 g | 0.92 |
| Glycine | 1 g | 0.09 |
| Sodium metabisulphite | 20 g | 1.83 |
| Camphor | 5 g | 0.46 |
| Calcium lactate | 10 g | 0.92 |
| KNO$_3$ | 19 g | 1.74 |
| | 1091 g | |

A test solution was prepared by admixing together the above ingredients and diluting a portion of the total composition with water to a concentration of 11 g/liter.

Two fresh cut Christmas trees were placed in the test solution and one was removed after 18 days. After 4 months, the tree allowed to remain in the test solution was still green with little needle drop whereas the tree removed from the test solution had turned brown and dropped all its needles.

EXAMPLE 7

Fifteen stems of yellow carnations were divided into three equal groups and each group was placed in a flask charged with 1 liter of working solution. One group (Group A) was placed in test solution A which did not contain caffeine, one group (Group B) was placed in test solution B which contained caffeine and one group (Control Group) was placed in water. The composition of the test solutions was as follows:

Test Solution A

| | | % by weight |
| --- | --- | --- |
| Glucose | 100.00 g | 87.49 |
| KNO$_3$ | 1.29 g | 1.13 |
| (NH$_4$)$_2$HPO$_4$ | 1.07 g | 0.94 |
| Gibberellic Acid (or GA$_3$) | 0.20 g | 0.17 |
| Citric Acid | 2.00 g | 1.75 |
| Tartaric Acid | 1.10 g | 0.96 |
| Mannitol | 3.00 g | 2.62 |
| Myo-inositol | 1.00 g | 0.87 |
| Glycine | 0.10 g | 0.09 |
| Sodium metabisulphite | 2.10 g | 1.84 |
| Camphor | 0.50 g | 0.44 |

Test Solution A (continued)

| | | % by weight |
| --- | --- | --- |
| Calcium Lactate | 1.84 g | 1.61 |
| Carbendazim | 0.10 g | 0.09 |
| | 114.30 g | |

The ingredients were admixed together and diluted before use with water to a concentration of 11 g/liter.

Test Solution B

| | | % by weight |
| --- | --- | --- |
| Glucose | 100.00 g | 86.42 |
| KNO$_3$ | 1.29 g | 1.11 |
| (NH$_4$)$_2$HPO$_4$ | 1.07 g | 0.92 |
| Gibberellic Acid (or GA$_3$) | 0.20 g | 0.17 |
| Citric Acid | 1.90 g | 1.64 |
| Tartaric Acid | 1.00 g | 0.86 |
| Mannitol | 3.00 g | 2.59 |
| Myo-inositol | 1.00 g | 0.86 |
| Glycine | 0.10 g | 0.09 |
| Sodium metabisulphite | 2.00 g | 1.73 |
| Camphor | 0.70 g | 0.60 |
| Calcium Lactate | 1.00 g | 0.86 |
| Carbendazim | 0.20 g | 0.17 |
| Nystatin | 0.05 g | 0.04 |
| Caffeine | 0.20 g | 0.17 |
| Oxine (8-hydroxyquinoline) | 2.00 g | 1.73 |
| | 115.71 g | |

The ingredients were admixed together and diluted before use with water to a concentration of 11 g/liter.

After one week, the stems in test solution B were clearly deeper in colour than the stems in test solution A or water, especially when examined in daylight. This clearly shows the effectiveness of caffeine as a colour stabiliser.

EXAMPLE 8

All flowering heads and coloured buds were removed from 25 strongly coloured star-gazer lilies, leaving only the green buds. Each stem was cut at its base. The stems were distributed amongst five flasks, each containing 800 ml of solutions A to D (defined in Table 3 below) or a water control; there were five stems in each solution. The concentration of the composition in each of the solutions A to D was 11 g/l. The volume of solution in each flask was replenished as necessary over the period of the experiment. The developmental state of the flowers and foliage was monitored over time with the results being shown in Table 4 (the % of starting buds remaining includes both unopened buds and flowers).

TABLE 3 continued onto the next page.

| Solutions/ components (g) | A | B | C | D |
| --- | --- | --- | --- | --- |
| Glucose | 100.00 | 100.00 | 100.00 | 100.00 |
| KNO$_3$ | 1.29 | 1.29 | 1.29 | 1.29 |
| (NH$_4$)$_2$HPO$_4$ | 1.07 | 1.07 | 1.07 | 1.07 |
| Gibberellic Acid (GA$_3$) | 0.21 | 0.21 | — | — |
| Citric Acid | 1.90 | 1.90 | 1.90 | 1.90 |

TABLE 3-continued continued onto the next page.

| Solutions/components (g) | A | B | C | D |
|---|---|---|---|---|
| Tartaric Acid | 1.00 | 1.00 | 1.00 | 1.00 |
| Mannitol | 3.00 | 3.00 | 3.00 | 3.00 |
| Myo-inositol | 1.00 | 1.00 | 1.00 | 1.00 |
| Glycine | 0.10 | 0.10 | 0.10 | 0.10 |
| Sodium Metabisulphite | 2.00 | 2.00 | 2.00 | 2.00 |
| Camphor | 0.70 | 0.70 | 0.70 | 0.70 |
| Calcium Lactate | 1.00 | 1.00 | 1.00 | 1.00 |
| Carbendazim | 0.20 | 0.20 | 0.20 | 0.20 |
| Nystatin | 0.05 | 0.05 | 0.05 | 0.05 |
| Caffeine | 0.41 | — | 0.41 | — |
| Theophylline | — | 0.21 | — | 0.21 |
| Oxine | 2.00 | 2.00 | 2.00 | 2.00 |

The results, shown in Table 4 below, emphasise the importance of gibberellic acid in prolonging the life of plant material. The depth of colour of blooms developed in solutions of gibberellic acid which also contain a methyl xanthine such as caffeine or theophylline are significantly deeper compared to the water control with the period for which colour is present also being extended. This experiment indicates that methyl xanthines enhance the bloom colour, prolong the period over which the blooms maintain their colour and cause colour to develop in unopened buds.

TABLE 4

| Day | A | B | C | D | Control |
|---|---|---|---|---|---|
| 5 | Healthy, strongly coloured flowers. Normally developing buds. | Healthy, strongly coloured flowers. Normally developing buds. | Wilting and some discoloured buds, flowers and leaves. | Wilting and some discoloured buds, flowers and leaves. | Senescing of flowers and leaves. Poorly developed, weakly coloured flowers. |
| 11 | 63% of starting buds remain. Strongly coloured flowers. Some signs of wilting. | 50% of starting buds remain. Strongly coloured flowers; less strongly coloured buds. Signs of wilting. | 11% of starting buds remain. Badly wilted. Some discoloured petals and leaves. | 30% of starting buds remain. Some wilted. Some discoloured petals and leaves. | 20% of starting buds remain. Slightly wilted, discoloured flowers. |
| 12–16 | Continued flowering. Good coloured flowers. | Flowerless or dead | Flowerless or dead | Flowerless or dead | Flowerless or dead |

EXAMPLE 9

Twenty Star-gazer lily stems were placed in flasks A to D; five stems in each flask. Solutions according to Table 5 were added to the flasks and the development of the lilies was monitored over a period of 19 days. Each lily head was categorised according 5 its stage of development: Green (G), green/white (G/W), white/green (W/G), white (W), white open (WO) and white very open (WVO). For white open (WO) the calyx has either just opened or the tips are no more than 2 cms apart.

TABLE 5 continued onto the next page.

| Solutions/components (g) | A | B | C | D |
|---|---|---|---|---|
| Glucose | 100.00 | 100.00 | 100.00 | 100.00 |
| $KNO_3$ | 1.29 | 1.29 | 1.29 | 1.29 |
| $(NH_4)_2HPO_4$ | 1.07 | 1.07 | 1.07 | 1.07 |
| Gibberellic Acid ($GA_3$) | 0.21 | 0.21 | — | — |
| Citric Acid | 1.90 | 1.90 | 1.90 | 1.90 |
| Tartaric Acid | 1.00 | 1.00 | 1.00 | 1.00 |
| Mannitol | 3.00 | 3.00 | 3.00 | 3.00 |
| Myo-inositol | 1.00 | 1.00 | 1.00 | 1.00 |
| Glycine | 0.10 | 0.10 | 0.10 | 0.10 |
| Sodium Metabisulphite | 2.00 | 2.00 | 2.00 | 2.00 |
| Camphor | 0.70 | 0.70 | 0.70 | 0.70 |
| Calcium Lactate | 1.00 | 1.00 | 1.00 | 1.00 |
| Carbendazim | 0.20 | 0.20 | 0.20 | 0.20 |
| Nystatin | 0.05 | 0.05 | 0.05 | 0.05 |
| Caffeine | 0.18 | — | 0.18 | — |
| Theophylline | — | 0.18 | — | 0.21 |
| Oxine | 1.97 | 1.97 | 1.97 | 1.97 |

The results arc shown in Table 6 below.

At 15 days all but 2 stems in each of flasks A and B had surviving very open white (WVO) flowers. All open or earlier buds present at day 4 had survived. One surviving very open white (WVO) flower from day 4 and one dead open white flower (WO) from each of flasks C and D was observed at day 15. The flowers in flasks C and D were deeper in colour than those in flask A. Flowers remained in flasks A and B only at 19 days. The flowers in flask B were deeper in colour than those in flask A.

These results further indicate the importance of gibberellic acid on prolonging the life of plant material and demonstrate that theophylline produces a stronger colour in the blooms than caffeine. In addition, it appears that the combination of caffeine and gibberellic acid both prolong the life and enhance the colour of the blooms.

TABLE 6

| Flask | G | | | | G/W | | | | W/G | | | | W | | | | WO | | | | WVO | | | |
|---|---|---|---|---|---|---|---|---|---|---|---|---|---|---|---|---|---|---|---|---|---|---|---|---|
| Day | 0 | 4 | 1 | 1 | 0 | 4 | 1 | 1 | 0 | 4 | 1 | 1 | 0 | 4 | 1 | 1 | 0 | 4 | 1 | 1 | 0 | 4 | 1 | 1 |
| Stem | | | 5 | 9 | | | 5 | 9 | | | 5 | 9 | | | 5 | 9 | | | 5 | 9 | | | 5 | 9 |
| A  1 | 1 | 1 | | | 1 | | | | | | | | 2 | 1 | 1 | | | | | | 2 | 2 | 2 | |
|    2 | 2 | | | | | | | | 1 | | | | | 1 | | | | 1 | | | 1 | 2 | 3 | 1 |
|    3 | 1 | | | | 1 | | | | | | | | | 1 | | | 1 | 1 | | | 1 | 2 | 2 | 1 |
|    4 | 1 | | | | 1 | | | | | 1 | | | 1 | 1 | | | | | | | | 1 | 3 | 1 |
|    5 | 1 | | | | 1 | | | | 1 | | | | | 1 | | | | | | | 1 | 3 | 2 | 1 |
| B  1 | 1 | | | | | | | | 1 | | | | | | | | 1 | 1 | | | 1 | 2 | 1 | 1 |
|    2 | 1 | | | | | | | | | | | | 1 | 1 | | | | 2 | | | | 3 | 2 | 1 |
|    3 | | | | | | | | | | | | | 1 | | | | | | | | 2 | 3 | 1 | 0 |
|    4 | 1 | | | | | | | | | | | | | 1 | | | | | | | 2 | 2 | 1 | 1 |
|    5 | 1 | | | | | | | | | | | | 1 | 1 | | | | | | | 2 | 3 | 2 | 0 |
| C  1 | 1 | | | | | | | | | | | | 2 | | | | 1 | 1 | | | | 3 | 1 | 0 |
|    2 | 1 | | | | | | | | | | | | | | | | 1 | 1 | | | 1 | 2 | | 0 |
|    3 | 2 | | | | | | | | 1 | | | | | | | | 1 | 1 | | | 1 | 2 | 2 | 0 |
|    4 | | | | | | | | | | | | | | | | | | | | | 3 | 3 | | 0 |
|    5 | 1 | | | | | | | | | | | | | | | | 1 | 1 | | | 1 | 2 | 1 | 0 |
| D  1 | 1 | | | | | | | | | | | | | | | | 1 | 1 | | | 1 | 3 | 1 | 0 |
|    2 | 1 | | | | 1 | | | | | | | | 1 | | | | | 2 | | | 1 | 2 | 1 | 0 |
|    3 | | | | | 1 | | | | | | | | | | | | | | | | 3 | 4 | | 0 |
|    4 | 1 | | | | | | | | 1 | | | | | | | | 1 | 1 | | | 2 | 2 | | 0 |
|    5 | 1 | | | | | | | | 1 | | | | 1 | | | | 1 | 1 | | | 3 | 1 | | 0 |

We claim:

1. A composition for promoting continued development of plant material and/or enhancing the flower color of plant material comprising a methyl xanthine and a gibberellin.

2. A composition according to claim 1, wherein the methyl xanthine is selected from the group consisting of caffeine and theophylline.

3. A composition according to claim 1 in which the gibberellin is gibberellic acid.

4. A composition for promoting continued development of plant material and/or enhancing the flower color of plant material comprising a methyl xanthine, a gibberellin and an osmotic pressure regulator.

5. A composition according to claim 4, wherein the methyl xanthine is selected from the group consisting of caffeine and theophylline.

6. A composition according to claim 4 wherein the gibberellin is gibberellic acid.

7. A composition for promoting continued development of plant material and/or enhancing the flower color of plant material comprising a methyl xanthine, a gibberellin and a chlorine sweep.

8. A composition according to claim 7 wherein the methyl xanthine is selected from the group consisting of caffeine and theophylline.

9. A composition according to claim 7 wherein the gibberellin is gibberellic acid.

10. A composition for promoting continued development of plant material and/or enhancing the flower color of plant material comprising a methyl xanthine, a gibberellin and a biocide.

11. A composition according to claim 10, wherein the methyl xanthine is selected from the group consisting of caffeine and theophylline.

12. A composition according to claim 10 wherein the gibberellin is gibberellic acid.

13. A composition for promoting continued development of plant material and/or enhancing the flower color of plant material comprising a methyl xanthine, a gibberellin and an agent which removes ethylene gas.

14. A composition according to claim 13, wherein the methyl xanthine is selected from the group consisting of caffeine and theophylline.

15. A composition according to claim 13 wherein the gibberellin is gibberellic acid.

16. A composition for promoting continued development of plant material and/or enhancing the flower color of plant material comprising a methyl xanthine, a gibberellin and a chelating agent.

17. A composition according to claim 16, wherein the methyl xanthine is selected from the group consisting of caffeine and theophylline.

18. A composition according to claim 16 wherein the gibberellin is gibberellic acid.

19. A composition according to claim 1 in dilute ready-to-use form.

20. A composition according to claim 1 in the form of a powder or tablet.

21. A composition according to claim 1 in the form of a liquid concentrate.

22. Plant material treated with a composition as defined in claim 1.

23. A method of enhancing the flower color of harvested plant material comprising treating harvested material with a composition comprising a methyl xanthine.

24. A method according to claim 23, wherein said methyl xanthine is selected from the group consisting of caffeine, theophylline and mixtures thereof.

25. A method according to claim 24, wherein said methyl xanthine is caffeine.

26. A method according to claim 24, wherein said methyl xanthine is theophylline.

27. A method of enhancing the flower color of plant material comprising treating the plant material with a composition comprising a methyl xanthine and a gibberellin.

28. A method according to claim 27, wherein said methyl xanthine is selected from the group consisting of caffeine, theophylline and mixtures thereof.

29. A method according to claim 28, wherein said methyl xanthine is caffeine.

30. A method according to claim 28, wherein said methyl xanthine is theophylline.

31. A method of enhancing the flower color of harvested plant material comprising treating harvested plant material with a composition comprising a methyl xanthine and a gibberellin.

32. A method according to claim 31, wherein the methyl xanthine is selected from the group consisting of caffeine, theophylline and mixtures thereof.

33. A method according to claim 32, wherein said methyl xanthine is caffeine.

34. A method according to claim 32, wherein said methyl xanthine is theophylline.

35. A composition for promoting continued development of plant material and/or enhancing the flower color of plant material comprising a methyl xanthine, a gibberellin and a pH regulator.

36. A composition according to claim 35, wherein the methyl xanthine is selected from the group consisting of caffeine and theophylline.

37. A composition according to claim 35, wherein the gibberellin is gibberellic acid.

38. A composition for promoting continued development of plant material and/or enhancing the flower color of plant material comprising a methyl xanthine, a gibberellin and a vitamin substrate.

39. A composition according to claim 38, wherein the methyl xanthine is selected from the group consisting of caffeine and theophylline.

40. A composition according to claim 38, wherein the gibberellin is gibberellic acid.

41. A composition for promoting continued development of plant material and/or enhancing the flower color of plant material comprising a methyl xanthine, a gibberellin and an amino acid.

42. A composition according to claim 41, wherein the methyl xanthine is selected from the group consisting of caffeine theophylline.

43. A composition according to claim 41, wherein the gibberellin is gibberellic acid.

44. A composition for promoting continued development of plant material and/or enhancing the flower color of plant material comprising a methyl xanthine, a gibberellin and a fluoride ion scavenger.

45. A composition according to claim wherein the methyl xanthine is selected from the group consisting of caffeine and theophylline.

46. A composition according to claim 45, wherein the gibberellin is gibberellic acid.

47. A composition for promoting continued development of plant material and/or enhancing the flower color of plant material comprising a methyl xanthine, a gibberellin and a source of nitrate or ammoniacal nitrogen.

48. A composition according to claim 47, wherein the methyl xanthine is selected from the group consisting of caffeine and theophylline.

49. A composition according to claim 48, wherein the gibberellin is gibberellic acid.

* * * * *

UNITED STATES PATENT AND TRADEMARK OFFICE
CERTIFICATE OF CORRECTION

PATENT NO. : 5,817,600
DATED : October 6, 1998
INVENTOR(S) : CARSTAIRS et al

It is certified that error appears in the above-identified patent and that said Letters Patent is hereby corrected as shown below:

Title page, item [63]    insert after "abandoned" the following: --which is a continuation-in-part of application Serial No. 08/545,677, filed October 31, 1995, now abandoned--.

Title page, left-hand column, insert prior to "[56]" the following:

--[30] Foreign Application Priority Data

May 1, 1993 [GB] United Kingdom 9309095.9

August 17, 1993 [GB] United Kingdom 9317063.1

April 29, 1994 [PCT] PCT/GB94/00923

Signed and Sealed this

Sixth Day of April, 1999

Attest:

Q. TODD DICKINSON

Attesting Officer

Acting Commissioner of Patents and Trademarks